United States Patent [19]

Roberts et al.

[11] Patent Number: 5,053,530

[45] Date of Patent: Oct. 1, 1991

[54] PREPARATION OF ISETHIONIC ACID WITH ORGANIC ACID

[75] Inventors: John S. Roberts, Bartlesville, Okla.; Harold W. Mark, Summerville, S.C.

[73] Assignee: Phillips Petroleum Company, Bartlesville, Okla.

[21] Appl. No.: 506,984

[22] Filed: Apr. 10, 1990

[51] Int. Cl.$^5$ .......................................... C07C 303/00
[52] U.S. Cl. .................................................. 562/108
[58] Field of Search ........................................ 562/108

[56] References Cited

U.S. PATENT DOCUMENTS 2,899,461  8/1959  Smith .
3,243,454  3/1966  Barrington et al. .
4,499,028  2/1985  Langley ............................... 562/108

FOREIGN PATENT DOCUMENTS 774563  5/1957  United Kingdom ................ 562/108

OTHER PUBLICATIONS

J. Chem. Soc. (London), 1942, pp. 716-718.
Chem. Eng. Handbook, Perry, 5th ed (1973), 16-7.

Primary Examiner—Alan Siegel
Attorney, Agent, or Firm—Ryan N. Cross

[57] ABSTRACT

Synthesis of isethionic acid comprising contacting an alkali metal isethionate and an organic acid.

8 Claims, No Drawings

PREPARATION OF ISETHIONIC ACID WITH ORGANIC ACID

BACKGROUND OF THE INVENTION

This invention relates to a new and useful improvement in the preparation of isethionic acid.

The preparation of isethionic acid is known in the art. Sexton et al, (U.S. Pat. No. 2,810,747) teaches preparing isethionic acid from its alkaline salt from ethylene oxide and potassium or sodium bisulfite using high pressure equipment. Furthermore, Smith, (U.S. Pat. No. 2,899,461) primarily teahes that alkali metal salts of isethionic acid can be prepared by reacting at least an equimolar proportion of ethylene sulfite and an alkali metal carbonate or bicarbonate. Additionally, Smith discloses that free isethionic acid can be obtained from its alkaline metal salt by acidfication with a mineral acid.

Smith is an improvement over Sexton, and is regarded as the state of the art process. However, the Smith method has many problems and drawbacks. In one experiment employing the Smith method, isethionic acid was prepared by reacting sodium isethionate with an acidic ion exhange resin. First, it was observed that the ion exhange resins have a low capacity for reacting with sodium isethionate—about 2-10 milliequivalent/gm. Second, it was also observed that due to the difficulty of converting a weak basic compound, sodium isethionate, into a strong acidic compound, isethionic acid, the equillibrium of the reaction favors the sodium isethionate. As the sodium ions ($Na^+$) displace hydrogen ions ($H^+$) in the reaction zone some of the unreacted sodium isethionate will eventually "break through" out of the reaction zone. The reaction zone must therefore be periodically regenerated with hydrogen ion ($H^+$) by the addition of a strong acid. One undesirable effect of this periodic reacidification procedure is that it leads to ion-exchange resin bead or particle breakage; which in turn results in an increase in the pressure drop across the reaction zone. Additionally, it results in an increase in downstream plugging. Third, this method is a very expensive method of preparing isethionic acid.

In view of the problems associated with the present state of the art, it is a desirable goal in the chemical industry to develop or discover a simple, improved and inexpensive process, that at a minimum, eliminates these problems and guarantees a better product yield.

SUMMARY OF THE INVENTION

It is a general object of this invention to provide a new, improved, and useful process for the preparation of isethionic acids which avoids the problems associated with the prior art methods.

It is another object of this invention to avoid the necessity for frequent regeneration of the reaction medium.

Another feature of this invention is to provide easy separation of the free isethionic acid in an aqueous medium from insoluble alkaline salts of the acid solvent.

In accordance with this invention isethionic acid is produced by contacting at least one alkaline earth metal or alkali metal isethionate salt with an organic acid.

DETAILED DESCRIPTION OF THE INVENTION

This invention is based on the discovery that insoluble alkaline earth metal and alkali metal salts of organic acids precipitate substantially into crystals much more readily than their mineral acid salts. This permits an easier separation and greater recovery of the free isethionic acid.

The invention can be carried out by contacting at least one isethionate salt with an organic acid in an aqueous medium and recovering isethionic acid from said aqueous medium. Such contacting in terms of the chemical ingredients can be represented by the chemical equation shown below:

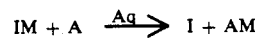

$$IM + A \xrightarrow{Aq} I + AM$$

IM = Isethionate salt i.e. of alkaline earth or alkali metal
A = Organic acid e.g. oxalic acid
I = Free isethionic acid
AM = Insoluble organic acid metal salt
Aq = Water Because of its high insolubility the organic acid metal salt will precipitate. Cooling the reaction mixture can be used to facilitate precipitation. The free isethionic acid can then be recovered by employing any suitable technique such as evaporating off the water.

Isethionate salts useful in this invention include salts of the alkaline earth metals such as calcium and magnesium, and salts of alkali metals such as potassium, lithium, and sodium. The alkali metal isethionates are preferred; and sodium isethionate is most particularly preferred.

Generally organic acids, especially those that will react to form an insoluble metal salt, such as monocarboxylic acids and dicarboxylic acids are useful in this invention. Suitable organic acids include those organic acids the metal salts of which are highly insoluble in water. Examples of such monocarboxylic acids are aldonic acid, gluconic acid, and mannonic acid. Preferred however, are dicarboxylic acids such as malonic acid, succinic acid, oxalic acid, adipic acid, and glutaric acid. Most distinctly preferred is oxalic acid.

The ratio of reactants useful in the practice of the invention is generally within the range of from about ½ to about 1½ moles of organic acid per mole of isethionate salt; it is preferred to use from about ¾ to about 1¼ moles of organic acid per mole of isethionate salt; and most preferred is about a 1:1 molar ratio of organic acid to isethionate salt.

Reaction temperature during the process of this invention varies. During the dissolution stage the temperature is generally in the range of from about 25° C. to about 100° C. During the crystallization stage the temperature is generally in the range of about −30° C. to about 25° C. The reaction time is generally from about 1 hour to about 20 hours depending on the desired yield and on the crystallization technique(s) used.

The contacting of the isethionate salt and organic acid necessary to effectuate this invention can be accomplished by employing suitable devices and methods known in art within the conditions recited in the above paragraphs.

CONTROL

This Run shows the process of the present state of the art in using mineral acids in the preparation of isethionic acid.

A solution of sodium isethionate (148.11 g, or 1.0 mole, in 150 mL of H$_2$O) in a flask was treated with 99.9 mL of concentrated hydrochloric acid solution (1.0 mole of HCL) by slowly adding HCL to the isethionate solution. The solution become cloudy when 90% of the HCL had been added, indicating that sodium chloride (NaCl) was beginning to crystallize. After adding all of the HCL, the mixture of reactants and products was transferred to a 2 L round bottom flask. The semisolid product was slurried in an adequate amount of MeOH to precipitate NaCL followed by filtration to remove th... e liquid... ion was then vacuum-stripped to remove methanol. Following evaporation of the methanol and water, the free isethionic acid remaining was weighed. It weighed 46.0 g (0.284 moles), representing a yield of about 28% from the starting sodium isethionate salt 148.11 g.

EXAMPLE I

This example illustrates that the inventive process represents a new and useful improvement over the present art in the preparation of isethionic acid.

A cloudy solution of sodium isethionate (370.3 g, or 2.5 moles dissolved in 250 mL of 100° C. H$_2$O) was mixed with oxalic acid solution (315.2 g, or 2.5 moles dissolved in 500 mL of 100° C. H$_2$O). This represents a 1:1 molar ratio. The combined solution was allowed to cool in an ice bath to promote crystallization. The crystals (sodium oxalate) were removed from the liquid by filtration. The free isethionic acid solution was then placed in a rotary evaporator to remove the water. A clear and extremely viscous isethionic acid, 384.2 g (2.37 moles) was obtained containing two moles of water of hydration representing a yield of about 94%. This represented a yield of more than three times that obtained when a mineral acid was used.

While this invention has been described in detail for the purpose of illustration, it is not to be construed as limited thereby but is intended to cover all changes and modifications within the spirit and scope thereof.

That which is claimed is:

1. A process for the preparation of isethionic acid comprising: contacting ... onate selected from the group consisting of alkali metal and alkaline earth metal isethionates with a carboxylic acid.

2. A process in accordance with claim 1 wherein said carboxylic acid is one the metal salts of which are highly insoluble in water.

3. A process in accordance with claim 1 wherein said alkali metal isethionate and said carboxylic acid are contacted in a range of about a 0.5:1 to about 1.5:1 molar ratio.

A process in accordance with claim 3 wherein said alkali metal isethionate and said carboxylic acid are contacted in about a 1:1 molar ratio.

5. A process in accordance with claim 1 wherein said isethionate is sodium isethionate.

6. A process in accordance with claim 1 wherein said carboxylic acid is chosen from the group consisting of monocarboxylic acid and dicarboxylic acids.

7. A process in accordance with claim 1 wherein said carboxylic acid is oxalic acid.

8. A process in accordance with claim 1 comprising the additional step of subjecting the resulting composition to a temperature it the range of about −30° C. to about 25° C. to thereby cause crystallization of undesired by-product.

* * * * *